United States Patent
Gomez-Mancilla

(10) Patent No.: US 6,503,920 B1
(45) Date of Patent: Jan. 7, 2003

(54) CABERGOLINE AND PRAMIPEXOLE: NEW USES AND COMBINATIONS

(75) Inventor: Baltazar Gomez-Mancilla, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/674,838

(22) PCT Filed: May 7, 1999

(86) PCT No.: PCT/US99/07024

§ 371 (c)(1),
(2), (4) Date: Nov. 6, 2000

(87) PCT Pub. No.: WO99/59563

PCT Pub. Date: Nov. 25, 1999

Related U.S. Application Data

(60) Provisional application No. 60/085,619, filed on May 15, 1998, and provisional application No. 60/087,943, filed on Jun. 4, 1998.

(51) Int. Cl.[7] ........................ A61K 31/44; A61K 31/425
(52) U.S. Cl. ........................................ 514/288; 514/367
(58) Field of Search .................................. 514/288, 367

(56) References Cited

U.S. PATENT DOCUMENTS 4,526,892 A * 7/1985 Salvati et al. ................ 514/288

OTHER PUBLICATIONS

LeWitt, P.A., "New Options for treatment of Parkinson's disease", Abstract to Baillieres Clinical Neurology, 6(1), pp. 109–123, Apr. 1997.*
Rabey, J. M. "Second Generation of Dopamine Agonists: Pros and Cons", Abstract to Journal of Neural Transmission. Supplementum, 45, pp. 213–214, Ref: 63, 1995.*
M. Asanuma, et al, *Rinsho–Sinkelgaku*, 33, pp 317–321, 1993.
DJ Burn, et al., *J. Neurol, Neurosurg. Psychiatry*, 57 (3), pp 278–284, 1994.
DJ Brooks, et al, *Ann Neurol*, 31, pp 184–192, 1992.
SJ Collins, et al, *J Neurol Neurosurg and Psychiatry*, 58, pp 167–173, 1995.
NL Foster, et al, *Neurology*, 39, pp 257–261, 1989.
J Ghinka, et al, *Neurology*, "Idzoxan treatment in progressive supranuclear palsy" 41, pp 986–991, 1991.
M Guttman, et al, *J Neurol Trans*, "L–Dopa Reverses the Elevated Density of D2 Dopamine Receptors in Parkinson's Disease Striatum", 64, pp 93–103, 1985.

M Guttman, et al, *Ann Neurol*, "Dopamine D2 Receptor Density Remains constant in Treated Parkinson's Disease," 19, pp 487–492, 1986.
JJ Hauw, et al, *Neurology*, "Preliminary NINDS neuropathologic criteria for Steele–Richardson–Olzewski syndrome," 44, pp 2015–2019, 1994.
JA Jackson, et al, *Ann Neurol*, "Progressive supranuclear palsy; Clinical features and response to treatment in 16 patients," 13, pp 273–278, 1983.
I Litvan, et al, *Oxford New York*, "Progressive Supranuclear Palsy: Clinical and research approaches," pp 254–269, 1992.
I Litvan, et al, *Ann Neurol*, "Pharmacological evaluation of the cholinergic system in progreissve supranuclear palsy," 36, pp 55–61, 1994.
T Maruyama, et al, *Rinso–Shinkeigaku*, "A Case of Progressive Supranuclear Palsy Dramatically Improved with L–threo–3,4–dihydroxyphenylserine (L–DOPS)," 32, pp 606–611, 1992.
J Mierau, et al, *Eur J Pharmacol*, "Biochemical and pharmacological studies on pramipexole a potent and selective dopamine D2 receptor agonist," 215, pp 161–170, 1992.
KA Neiforth, et al, *Clin Neuropharm*, "Retrospective study of drug response in 87 patients with progressive supranuclear palsy," 16, pp 338–346, 1993.
A Neophytides, et al, *Neurol Neurosurg Psych*, "The use of lisuride, a potent dopamine and serotonin agonist, in the treatment of progressive supranuclear palsy," 45, pp 261–263, 1982.
J Pascual, et al, *Ann Neurol*, "Dopamine D1 and D2 receptros in progressive supranuclear palsy; An autoradiographic study," 332, pp 703–707, 1992.
L Peirot, et al, *J Neurol Sci*, d1 and D2 type dopamine receptors in patients with Parkinson's disease and progressive supranuclear palsy, 86, pp 291–306, 1988.
AC Williams, et al, *Oxford: Pergamon Press*, "Actions of bromocriptine in the Shy–Drager and Steele–Richardson–Olszewski syndromes", K.Fuxe, D.B.Cane, eds. "Dopaminergic Ergot Derivatives and Motor Function", pp 271–283, 1979.

* cited by examiner

*Primary Examiner*—Dwayne C. Jones
(74) *Attorney, Agent, or Firm*—Austin W. Zhang

(57) ABSTRACT

This invention discloses new uses and treatments involving cabergoline, pramipexole and new combinations of cabergoline plus pramipexole used to treat patients. Here we disclose the use of cabergoline or pramipexole to treat PSP and MSA. Also disclosed is a combination treatment of cabergoline and pramipexole provided concurrently to a patient in need thereof for the treatment of various central nervous system diseases and in particular for the treatment of Parkinson's Disease (PD), but also for PSP and MSA.

10 Claims, No Drawings

CABERGOLINE AND PRAMIPEXOLE: NEW USES AND COMBINATIONS

This application is the national phase of International Application PCT/US99/07024 filed May 7, 1999.

This application claims benefit of Provisional Application Ser. No. 60/085,619 filed May 15, 1998, which claims benefit of Ser. No. 60/087,943 filed Jun. 4, 1998.

FIELD OF THE INVENTION

This invention relates to the field of diseases and treatments for central nervous system disorders (CNS), specifically to treatments involving cabergoline and pramipexole.

INFORMATION DISCLOSURE

M. Asanuma, H. Hirata, Y. Kondo and N. Ogawa. A case of progressive supranuclear palsy showing marked improvements of frontal hypoperfusion, as well as parkinsonism with amitriptyline. *Rinsho-Shinkeigaku March* 1993 Vol. 33 (3) pp. 317–321.

Burn D. J., Sawle G. V., and Brooks D. J. "Differential Diagnosis of parkinson's Disease, Multiple System Atrophy, and Steele-Richardson-Olszewski syndrome: Discriminant Analysis of Striatal 18F-dopa PET data." J. Neurol. Neurosurg. Psychiatry March 1994 Vol. 57 (3), pp. 278–284.

Brooks D J, Ibanez V, Sawle G V et al. Striatal D2 receptor status in patients with Parkinson's disease, striatonigral degeneration, and progressive supranculear palsy measured with [11C]-raclopride and positron emission tomography. Ann Neurol 1992;31:184–192.

Collins S J, Ahlskog J E, Parisi J E, and Maraganore D M. Progressive supranuclear palsy: neuropathologically based diagnostic clinical criteria. J Neurol Neurosurg and Psychiatry 1995;58:167–173.

Foster N L, Aldrich M S, Bluemlein L, et al. Failure of cholinergic agonist RS-86 to improve cognition and movement in PSP despite effects on sleep. Neurology 1989;39:257–261.

Ghika J, Tennis M, Hoffman E, et al. Idzoxan treatment in progressive supranuclear palsy. Neurology 1991;41:986–991.

Guttman M, Seeman P. L-Dopa Reverses the Elevated Density of D2 Dopamine Receptors in Parkinson's Diseased Striatum. J Neural Trans 1985;64:93–103.

Guttman M, Seeman P, Reynolds G P, Riederer P, Jellinger K, Tourtellotte W W. Dopamine D2 Receptor Density Remains Constant in Treated Parkinson's Disease. Ann Neurol 1986;19:487–492.

Hauw J J, Daniel S E, Dickson E. et al. Preliminary NINDS neuropathologic criteria for Steele-Richardson-Olszewski syndrome (progressive supranuclear palsy). Neurology 1994;44:2015–2019.

Jackson J A, Jankovic J, Ford J. Progressive supranuclear palsy: Clinical features and response to treatment in 16 patients. Ann Neurol 1983;13:273–278.

Litvan I, Chase T N. Traditional and experimental therapeutic approaches. In: Progressive Supranuclear Palsy: Clinical and research approaches. Ed. Litvan I and Agid Y. Oxford, N.Y. 1992, pp. 254–269.

Litvan I, Blesa R, Clark K, etal. Pharmacological evaluation of the cholinergic system in progressive supranuclear palsy. Ann Neurol 1994;36:55–61.

Maruyama T, Tamaru F, Yamagisawa N, A Case of Progressive Supranuclear Palsy Dramatically Improved with L-threo-3,4-dihydroxyphenylserine (L-DOPS). Rinso-Shinkeigaku June 1992, Vol:32(6), pp. 606–611.

Mierau J, Schingnitz G. Biochemical and pharmacological studies on pramipexole a potent and selective dopamine D2 receptor agonist. Eur J Pharmacol 1992;215:161–170.

Neiforth K A Golbe L I. Retrospective study of drug response in 87 patients with progressive supranuclear palsy. Clin Neuropharm 1993;16:338–346.

Neophytides A, Lieberman A N, Goldstein M, etal. The use of lisuride, a potent dopamine and serotonin agonist, in the treatment of progressive supranuclear palsy. J Neurol Neurosurg Psych 1982:45:261–263.

Pascual J, Berciano J, Grijalba B, et al. Dopamine D1 and D2 receptros in progressive supranuclear palsy: An autoradiographic study. Ann Neurol 1992;332–703–707.

Peirot L, Desnos C, Blin J, et al. D1 and D2-type dopamine receptors in patients with Parkinson's disease and progressive supranuclear palsy. J Neurol Sci 1988;86:291–306

Williams A C, Nutt J, Lake C R et al. Actions of bromocriptine in the Shy-Drager and Steele-Richardson-Olszewski syndromes. In: K. Fuxe, D. B. Calne, eds. Dopaminergic Ergot Derivatives and Motor Function. Oxford: Pergamon Press 1979, pp. 271–283.

SUMMARY OF THE INVENTION

This invention discloses new uses and treatments involving cabergoline, pramipexole and new combinations of cabergoline plus pramipexole. Here we disclose the use of cabergoline or pramipexole to treat PSP and MSA. Also disclosed is a combination treatment of cabergoline and pramipexole provided concurrently or in alternating fashion to a patient in need thereof for the treatment of various central nervous system diseases and in particular for the treatment of Parkinson's Disease (PD), but also for PSP and MSA.

ADDITIONAL DESCRIPTION OF THE INVENTION

Cabergoline is the generic name for the active ingredient in DOSTINEX® Tablets, sold in the United States as a treatment for hyperprolactinemic disorders, and CABASER®, sold in Europe as a treatment for Parkinson's disease. The synthesis and use of cabergoline is disclosed and claimed in U.S. Pat. No. 4,526,892, which is incorporated herein by reference. The chemical name for the compound is 1[(6-allylergolin-8β-yl)-carbony.]-1-[3-(dimethylamino)propyl]-3-ethylurea. Cabergoline, and its pharmaceutical salts, are the most preferred of one part of the combination of drugs of this invention but all of the compounds disclosed in U.S. Pat. No. 4,526,892, should also be considered useful drugs that are one part of the different classes of drugs that comprise this invention.

Cabergoline has the following structural formula.

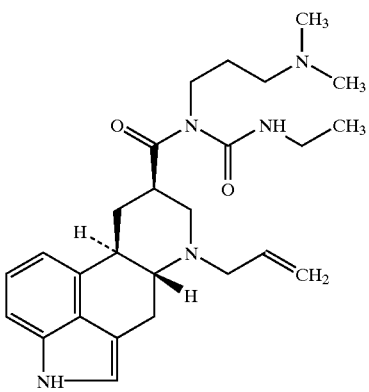

Conventional pharmaceutical preparations of cabergoline can be used, e.g., consisting essentially of an inert pharmaceutical carrier and an effective dose of the active substance: e.g., plain or coated tablets, capsules, lozenges, powders, solutions, suspensions, emulsions, syrups, suppositories, etc. Tablets are preferred.

CABASER®, is marketed by Pharmacia & Upjohn Inc., a major pharmaceutical company. A package insert describing CABASER®, its pharmacokinetics, Parkinson's disease patients, clinical studies, indications and usage, contraindication and warnings is provided by Pharmacia & Upjohn. This package insert and its descriptions are incorporated by reference into this application.

The dose response for both efficacy and side effects appears to be mainly linked to individual sensitivity. Obtain dose optimization through slow initial dose titration, from starting doses of 0.5 mg ("de novo"patients) to 1 mg (patients taking other dopamine-agonists). In patients already receiving levodopa, gradually decrease the levodopa dosage while increasing the dosage of CABASER, until the optimum balance is determined. In view of the long-lasting kinetics of cabergoline, adjust the daily dose at weekly (initial weeks) or biweekly intervals using increments of 0.5 to 1 mg, up to optimal doses.

The recommended therapeutic dosage is 2 to 4 mg daily as monotherapy in newly diagnosed patients and 2 to 6 mg daily as adjuvant therapy to levodopa/carbidopa. Give CABASER as a single daily dose. Maximum doses higher than 6 mg daily and up to 20 mg daily have been administered in a small proportion of patients exposed to the drug during preregistration studies.

Under some circumstances and with the appropriate patients the dosage level of cabergoline is where the initial dose of cabergoline is administered to the patient at a dose of 0.5 to 1 mg/patient/day and is adjusted upward at weekly intervals to a therapeutic dosage of 2, 4, 6, 8 or 10 mg/patient/day.

Safety and efficacy have not been investigated in children.

The precise dosage would be determined by the treating physician evaluating such factors are the progression of the state of the disease, the weight and age of the patient, whether and to what extent other drugs such as L-Dopa or levodopa were administered, and other such factors as are typically evaluated by a physician before determining the dosage of a CNS drug to be administered to a patient Pramipexole dihydrochloride monohydrate (pramipexole) is the generic name for the active ingredient of Mirapex®. This compound in also known by the chemical names 2-amino-6-n-propyl-amino-4,5,6,7-tetrahydrobenzothiazole dihydrochloride monohydrate and (S)-2-amino-4,5,6,7-tetrahydro-6propylamino-2,6-benzothiazole dihydrochloride monohydrate. The compound and structurally related analogs are claimed in U.S. Pat. No. 4,886,812, incorporated by reference. Pramipexole, pharmaceutically acceptable acid addition salts, including the dihydrochloride, are the most preferred of one part of the combination of drugs of this invention but all of the compounds disclosed in U.S. Pat. No. 4,886,812 should also be considered useful drugs that are one part of the different classes of drugs of this invention.

Pramipexole has the following structural formula.

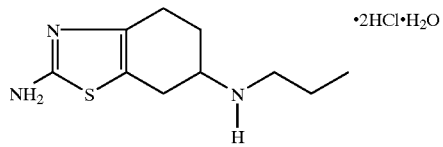

Conventional pharmaceutical preparations of pramipexole, can be used, e.g., consisting essentially of an inert pharmaceutical carrier and an effective dose of the active substance; e.g., plain or coated tablets, capsules, lozenges, powders, solutions, suspensions, emulsions, syrups, suppositories, etc. Tablets are preferred.

Mirapex® (pramipexole) is marketed by Pharmacia & Upjohn Inc., a major pharmaceutical company. Mirapex® has been approved by the U.S. Food and Drug Administration (F.D.A) and package insert describing Mirapex®, its pharmacokinetics, Parkinson's disease patients, clinical studies, indications and usage, contraindication and warnings is provided by Pharmacia & Upjohn. This package insert and its descriptions are incorporated by reference into this application.

The preferred dosages of pramipexole when used as disclosed in this invention, as a combination or concurrent drug administered with cabergoline are the same dosages as disclosed in the package insert mentioned above. Dosage should be initiated at a subtherapeutic level to avoid intolerable adverse effect and orthostatic hypotension. Mirapex® should be titrated gradually in all patients, starting from 0.375 mg/day in patients with normal renal function given in three divided doses and should not be increased more frequently than every 5 to 7 days. Ascending dosage schedules can be found on the package insert. Maintenance treatment can be effective over a broad range and but is recommended over a range of 1.5 to 4.5 mg/day, administered in equally divided doses three times a day. The effective dose range can be from 0.1 to 10 mg/day/patient, preferabley 2–8 mg/day/patient and more preferably between 2 and 5 mg/day/patient.

Under some circumstances and with the appropriate patients the initial dose of pramipexole is administered to the patient at a dose of 0.5 to 1.0 or preferably 0.375 mg/patient/day and is adjusted upward every 5 to 7 days to a therapeutic dosage of 3, 4, 5, 6, or 7 mg/patient/day.

Dosages should be increased gradually. Providing patients do not experience intolerable side effects, the dosage should be titrated to achieve a maximal therapeutic effect.

The precise dosage would be determined by the treating physician evaluating such factors are the progression of the state of the disease, the weight and age of the patient, whether and to what extent other drugs such as L-Dopa or levodopa were administered, and other such factors as are typically evaluated by a physician before determining the dosage of a CNS drug to be administered to a patient.

Part I

The first aspect of this invention discloses a combination of drugs useful in the treatment of various central nervous system diseases and in particular for the treatment of Parkinson's Disease (PD). The two drugs to be combined are cabergoline and/or its derivatives and pramipexole and/or its derivatives.

The concomitant or concurrent treatment disclosed here requires that both cabergoline and pramipexole be administered to a patient suffering from a CNS disease. The dosages would be about the same as indicated above for each drug and each drug would typically be administered separately. The drugs can be administered in separate or combined forms (single tablet or capsule), they can be administered so that some of both drugs are in the patient during any 24 hour period or the administration of the drugs can staggered with each drug being given every other 24 hours, alternating with the other drug. The drugs can be given with or without the administration of levodopa. Levodopa can be given at a dose of approximately 800 mg/day but reduction of levodopa dosage should be considered. The dosages provided here are not intended to guide a practitioner but rather are only intended to describe the invention. Proper precautions should be taken and no CNS drug should be given unless under the direction and supervision of a physician.

Concurrent treatment is especially effective at treating patents with advance forms of PD but it is also effective at treating milder forms of the disease.

The treatment disclosed here provides special benefits to the patient. For the first time a drug treatment system is provided that helps control a PD patients' entire system, including both pre and post synaptic cells. Cabergoline is a preferred D2 agonist and pramipexole is a preferred D3 agonist. Providing the two drugs to a patient concurrently gives the patients surprising and unexpected relief from the symptoms of Parkinson's Disease. Here pramipexol provides protective relief, that is pre synaptic effect protection and therapy at the same time that cabergoline provides post synaptic affects and acts as a dopamine enhancing or replacing agent.

In another embodiment of this invention, pramipexole is provided to a patient before the administration of cabergoline. A patient is started with pramipexole, later when efficacy makes it necessary, the patient is also treated with cabergoline. Alternatively, a patient may be started with pramipexole and also a very low dose of cabergoline, which is less well tolerated than pramipexole. The cabergoline can then be titrated with the goal of reaching optimal dosage as the beneficial effects of pramipexol tend to plateau.

A preferred combination of drugs and dosages would be with a combination of up to 18 mg of cabergoline and up to 8 mg of pramipexole. More preferred would be up to 12 mg of cabergoline and up to 5 mg of pramipexole. Depending upon the patients, and after titrating up from a low dose, most preferred might be providing a patient up to 8 mg of cabergoline and up to 5 mg of pramipexole, with or without levodopa.

Note that l-Dopa or levodopa may also be provided in conjunction with the combination of cabergoline and pramipexole.

Without any additional description it is believed the invention is fully described above. The following example, below, is provided to illuminate the invention without restricting it in any way.

Four patients with advanced Parkinson's Disease were provided with a combination of up to 12 mg of cabergoline, up to 5 mg of pramipexole and a low dosage of 300 mg of l-Dopa or levodopa. In all cases in the opinion of the investigator symptoms showed significant improvement.

Part II

In a second aspect of this invention it is disclosed that either cabergoline or pramipexole, or the combination, can be used to treat patients having symptoms of two diseases that are not typically treated with a D2 agonist. Those diseases are Progressive Supranuclear Palsy (PSP) and Multisystemic Atrophy or MSA.

PSP is a neurodegenerative disease of unkown etiology first described in 1964 by Steele, Richardson and Olszewski J, Arch. Neurol. 1964; 10:333–359. PSP is also known as Steele-Richardson-Olszewski syndrome. See, Manyo Y., "Steele-Richardson-Olszewski syndrome" Nippon-Rinsho November 1993, Vol. 51 (11), pp. 2962–2967. The syndrome usually begins in the seventh deceade and is characterized by postural instability, gaze palsy, mental changes, and parkinsonian signs such as bradykinesia and rigidity. It has a rapid and severe course of illness.

PSP is a relentlessly progressive neurodegenerative disease characterized by postural instability, rigidity, bradykinesia, bulbar dysfunction and loss of control of voluntary eye movements. It causes progressive disability and death, usually within six years of diagnosis. PSP has many features in common with Parkinson's disease, a disorder with which it is often mistaken. It has been estimated that PSP progresses more rapidly than Parkinson's Disease. The life span for Parkinson's Disease patients has been estimated to be between 15–20 years after the diagnosis has been made. The life span for PSP patients has been estimated to be less than 6 years. PSP patients have several systems affected (dopamine, 5-HT, Ach) and the progression of neuron decrease is unknown. Parkinson's Disease patients have mainly the dopaminergic system affected, however, the 5-HT, and Ach are affected to a lesser degree. Unlike Parkinson's disease, however, good treatment strategies are currently lacking for PSP.

PSP is associated with neuropathological changes in the substantia nigra, caudate, putamen, globus pallidum, subthalamic nucleus as well as a number of brainstem nuclei (Hauw et al. 1994). Postmortem neurochemical analysis has shown specific changes in PSP different than those found in Parkinson's Disease (PD) (Kish et al. 1985). Striatal dopamine depletion is severe and is similar in magnitude when compared to patients with Parkinson's disease. This is most likely responsible for the parkinsonian symptoms that most patients report. PSP patients: however, do not show the regional variation in dopamine depletion seen in PD. In PSP both the caudate nucleus and putamen have severe dopamine depletion, whereas in the PD the putamen has a great reduction. Serotonin is not diminished in the striatum of PSP patients but is reduced by approximately 50% in PD. Markers of striatal cholinergic neurons are reduced in PSP due to the cholinergic cell loss but this is not the case in PD. This may account for the cognitive changes in these patients. Striatal norepinephrine levels are not changed in PSP.

Dopamine receptors have been studied in postmortem PD and PSP brains (Pierot et al 1988) and in vivo with PET and SPECT. Dopamine D-2 receptors are elevated in untreated PD patients using homogenate radioreceptor assays (Guttman and Seeman, 1985). This supersensitivity is reversed with treatment (Guttman et al 1986). In vivo imaging studies have confirmed these findings (Brooks et al 1992). In PSP, however, there is a reduction in receptor binding compared to controls. The magnitude of the reduction is variable with reports of 15–50% change (Pascual et al 1990). PE studies with raclopride (Brooks et al, 1992) have confirmed reduced binding in the striatum. These changes in the imaging studies are not specific for PSP since other forms of secondary Parkinsonism have similar findings including Multisystem Atrophy. Dopamine D-1 receptors are not reduced as measured by postmortem studies in PSP (Pascual et al 1992). There has been speculation that the reduction of D-2 receptors may be partially responsible for the therapeutic failure of dopaminergic replacement therapy. Since the reduction observed in some studies is minimal it is unclear what this effect is.

Despite PSP being one of the most common secondary forms of parkinsonism, there has been little in the way of formalized trials to assess therapy in this condition. Litvan and Chase have reviewed all of the published reports in PSP and have summarized the results (Litvan and Chase 1992). They comment that the literature is difficult to interpret because of the lack of controlled clinical trials. Three hundred and eighty-one patients have been reported between 1965–1990. Golbe has retrospectively reviewed their therapeutic experience in 83 PSP patients and concluded that L-dopa therapy was the most effective treatment (Nieforth and Golbe, 1993). Dosage ranged from 750–1500 mg per day and the response rate was 54% showing mild to moderate improvement on the basis of clinical impressions with 44% showing no effect. The response to treatment has been variable and many authors suggest that if patients respond, that this response is not robust and is usually transient. Most patients are offered L-dopa combination medication such as Sinemet or Prolopa and are titrated to higher doses compared to PD patients. Since the response to L-dopa is not impressive some algorithms for diagnostic classification of PSP use the lack of response to L-dopa as part of the criteria for making the diagnosis (Collins et al 1995). The most common side effects that have been reported are the development of hallucinations (Litvan and Chase 1992). It is interesting to note the L-dopa induced dyskinesias have not been reported. Dopamine agonists have been used to treat a small number of PSP patients (Litvan and Chase 1992). Bromocriptine was prospectively examined in a double-blind, placebo controlled clinical trial in 9 subjects (Williams et al 1979). This study failed to show any significant improvement in 6/9 subjects in doses up to 90 mg/day. The remaining 3 had modest improvement in their parkinsonian symptoms. In other studies, approximately 25% of subjects responded with improvement in their parkinsonian features. One should note that in PD, bromocriptine monotherapy has not been successful in treating most patients. Pergoline has also been used in a small number of patients. In a controlled trial, 2/3 subjects has mild antiparkinsonian effects (Jackson et al 1983). This may be due to the higher potency of this drug compared to bromocriptine and its agonist effects on D-1 receptors. Lisuride treatment has been studied in a small number of PSP patients. Neophytides found that in a controlled trial of 7 subjects that there was not any significant results and two patients had a mild improvement (Neophytides et al 1982).

In an attempt to improve cholinergic neurotransmission, cholinergic agonists have been used to treat subjects with PSP. Foster reported no consistent motor or cognitive changes in 10 patients in a double blind crossover study with RS-86 which is a relatively nonselective M1 an M2 agonist (Foster et al 1989). Litvan and used physostigmine in a small number of PSP patients in a double blind crossover study. They did not show any improvement in parkinsonian, extraocular or pseudobulbar symptoms (Litvan et al 1994). Idazoxan is an experimental alpha adrenergic antagonist. It has been used in a 2-week open label study at a dose of 120 mg/day in two patients (Ghika et al 1991). There was a marginal improvement ranging from 12–34% in these subjects but sympathetic side effects were common.

The dosage level of cabergoline to treat either of these diseases PSP or MSA is the same dose provided above for the treatment of Parkinson's Disease.

Multisystemic atrophy or MSA. A description of MSA appears in Burn D. J., Sawle G. V., and Brooks D. J. "Differential Diagnosis of parkinson's Disease. Multiple System Atrophy, and Steele-Richardson-Olszewski syndrome: Discriminant Analysis of Striatal 18F-dopa PET data." J. Neurol. Neurosurg. Psychiatry March 1994 Vol. 57 (3), pp. 278–284, incorporated by reference herein.

What is claimed is:

1. A method for treating patients suffering from progressive supranuclear palsy comprising the administration of a therapeutic amount of cabergoline or a pharmacologically acceptable salt thereof.

2. A method for treating patients suffering from multisystemic atrophy comprising the administration of a therapeutic amount of cabergoline or a pharmacologically acceptable salt thereof.

3. The method of claim 2 where the cabergoline is administered to the patient at an initial dose of 0.5 to 1 mg/patient/day and is adjusted upward at weekly intervals to a therapeutic dosage of 2, 4, 6 or 8 mg/patient/day.

4. The method of claim 3 where the cabergoline dose is 4–6 mg per day.

5. A method for treating patients suffering from progressive supranuclear palsy comprising the administration of a therapeutic amount of pramipexole or a pharmacologically acceptable salt thereof.

6. The method of claim 5 where the pramipexole is administered to the patient at an initial dose of 0.5 to 1 mg/patient/day and is adjusted upward at weekly intervals to a therapeutic dosage of 3, 4, 5 or 6 mg/patient/day.

7. The method of claim 6 where the initial dose of pramipexole is 0.375 mg/patient/day and the therapeutic dose is 5 mg/patient/day.

8. A method for treating patients suffering from multisystemic atrophy comprising the administration of a therapeutic amount of pramipexole or a pharmacologically acceptable salt thereof.

9. The method of claim 8 where the pramipexole is administered to the patient at a dose of 0.5 to 1 mg/patient/day and is adjusted upward at weekly intervals to a therapeutic dosage of 3, 4, 5 or 6 mg/patient/day.

10. The method of claim 9 where the dose is 5 mg per day.

* * * * *